United States Patent
Montserrat Carreras et al.

(10) Patent No.: US 9,802,990 B2
(45) Date of Patent: Oct. 31, 2017

(54) FUNCTIONAL PEPTIDES FOR OBESITY DISORDERS

(71) Applicant: DANONE, S.A., Barcelona (ES)

(72) Inventors: Agusti Montserrat Carreras, Llinars del Valles (ES); Cristina Alvarez Fernandez, Cerdanyola del Valles (ES); Montserrat Andreu Corominas, Sant Climent del Llobregat (ES); Daniel Ramón Vidal, La Eliana (ES); Esther Bataller Leiva, Paterna (ES); Patricia Martorell Guerola, Picassent (ES); Salvador Genovés Martínez, Aldaia (ES)

(73) Assignee: DANONE, S.A., Barcelona (ES)

(*) Notice: Subject to any disclaimer, the term of this patent is extended or adjusted under 35 U.S.C. 154(b) by 66 days.

(21) Appl. No.: 14/768,823

(22) PCT Filed: Feb. 19, 2013

(86) PCT No.: PCT/EP2013/053233
§ 371 (c)(1),
(2) Date: Aug. 19, 2015

(87) PCT Pub. No.: WO2014/127798
PCT Pub. Date: Aug. 28, 2014

(65) Prior Publication Data
US 2016/0002303 A1 Jan. 7, 2016

(51) Int. Cl.
| | |
|---|---|
| A61K 38/00 | (2006.01) |
| A61P 3/04 | (2006.01) |
| A61P 39/06 | (2006.01) |
| C12P 21/04 | (2006.01) |
| C07K 5/00 | (2006.01) |
| C07K 7/00 | (2006.01) |
| C07K 16/00 | (2006.01) |
| C07K 17/00 | (2006.01) |
| A61K 38/04 | (2006.01) |
| C07K 14/415 | (2006.01) |
| A61K 38/08 | (2006.01) |
| C07K 14/47 | (2006.01) |
| A61K 38/10 | (2006.01) |
| A61K 38/16 | (2006.01) |
| A61K 36/48 | (2006.01) |
| A23L 33/18 | (2016.01) |

(52) U.S. Cl.
CPC ............ *C07K 14/415* (2013.01); *A23L 33/18* (2016.08); *A61K 36/48* (2013.01); *A61K 38/08* (2013.01); *A61K 38/10* (2013.01); *A61K 38/168* (2013.01); *C07K 14/4703* (2013.01); *A23V 2002/00* (2013.01); *A23Y 2220/63* (2013.01); *A23Y 2240/75* (2013.01); *A61K 38/00* (2013.01)

(58) Field of Classification Search
None
See application file for complete search history.

(56) References Cited

U.S. PATENT DOCUMENTS

2006/0204617 A1* 9/2006 Hauser ............... A23C 9/1315
426/52

FOREIGN PATENT DOCUMENTS

| ES | WO 2011110884 A1 * | 9/2011 | ........... A61K 35/744 |
|---|---|---|---|
| JP | 2004-99447 A | 4/2004 | |
| WO | 2008/131008 A2 | 10/2008 | |

OTHER PUBLICATIONS

Gonzalez de Mejia et al. "Fatty acid synthase and in vitro adipogenic response of human adipocytes inhibited by alpha and alpha' subunits of soybean beta-conglycinin hydrolysates" Food Chem. 119:1571-1577. Published 2010.*
Yun J "Possible anti-obesity therapeutics from nature—A review" Phytochemistry 71:1625-1641. Published Aug. 21, 2010.*
Wang W and Gonzalez de Mejia "A New Frontier in Soy Bioactive Peptides that May Prevent Age-related Chronic Diseases" Comprehensive Reviews in Food Science and Food Safety 4:63-78. Published 2005.*
Jong Won Yun, et al. "Possible anti-obesity therapeutics from nature—A review", Phytochemistry, Oct. 2010, pp. 1625-1641, vol. 71, No. 14-15.
M. Lunder, et al., "Peptide inhibitor of pancreatic lipase selected by phage display using different elution strategies", Journal of Lipid Research, 2005, pp. 1512-1516, vol. 46.
Written Opinion for PCT/EP2013/053233 dated Jun. 19, 2013 [PCT/ISA/237].
International Search Report for PCT/EP2013/053233 dated Jun. 19, 2013 [PCT/ISA/210].

* cited by examiner

*Primary Examiner* — Christina Bradley
*Assistant Examiner* — Zachary J Miknis
(74) *Attorney, Agent, or Firm* — Sughrue Mion, PLLC

(57) ABSTRACT

The present invention concerns certain peptides obtainable by hydrolysis from soy glycinin by the action of supernatant cultures of strains belonging to the genera *Lactobacillus* or *Streptococcus*. These peptides, extracts containing them and food products containing them are useful for the treatment and/or prevention of obesity and oxidative stress.

8 Claims, 2 Drawing Sheets

SEQUENCE LISTING

<160> NUMBER OF SEQ ID NOS: 22

<210> SEQ ID NO 1
<211> LENGTH: 10
<212> TYPE: PRT
<213> ORGANISM: Glycine soja
<220> FEATURE:
<223> OTHER INFORMATION: EEEGGSVLSG

<400> SEQUENCE: 1

Glu Glu Glu Gly Gly Ser Val Leu Ser Gly
1               5                   10

<210> SEQ ID NO 2
<211> LENGTH: 6
<212> TYPE: PRT
<213> ORGANISM: Glycine soja
<220> FEATURE:
<223> OTHER INFORMATION: SDNFEY

<400> SEQUENCE: 2

Ser Asp Asn Phe Glu Tyr
1               5

<210> SEQ ID NO 3
<211> LENGTH: 14
<212> TYPE: PRT
<213> ORGANISM: Glycine soja
<220> FEATURE:
<223> OTHER INFORMATION: EEDQPRPDHPPQRP

<400> SEQUENCE: 3

Glu Glu Asp Gln Pro Arg Pro Asp His Pro Pro Gln Arg Pro
1               5                   10

<210> SEQ ID NO 4
<211> LENGTH: 8
<212> TYPE: PRT
<213> ORGANISM: Glycine soja
<220> FEATURE:
<223> OTHER INFORMATION: SVIKPPTD

<400> SEQUENCE: 4

Ser Val Ile Lys Pro Pro Thr Asp
1               5

<210> SEQ ID NO 5
<211> LENGTH: 16
<212> TYPE: PRT
<213> ORGANISM: Glycine soja
<220> FEATURE:
<223> OTHER INFORMATION: QGENEEEDSGAIVTVK

<400> SEQUENCE: 5

Gln Gly Glu Asn Glu Glu Glu Asp Ser Gly Ala Ile Val Thr Val Lys
1               5                   10                  15

<210> SEQ ID NO 6
<211> LENGTH: 14
<212> TYPE: PRT
<213> ORGANISM: Glycine soja
<220> FEATURE:
<223> OTHER INFORMATION: QGENEGEDKGAIVT

<400> SEQUENCE: 6

Gln Gly Glu Asn Glu Gly Glu Asp Lys Gly Ala Ile Val Thr
1               5                   10

-continued

```
<210> SEQ ID NO 7
<211> LENGTH: 17
<212> TYPE: PRT
<213> ORGANISM: Glycine soja
<220> FEATURE:
<223> OTHER INFORMATION: QDEDEDEDEDKPRPSRP

<400> SEQUENCE: 7

Gln Asp Glu Asp Glu Asp Glu Asp Glu Asp Lys Pro Arg Pro Ser Arg
1               5                   10                  15

Pro

<210> SEQ ID NO 8
<211> LENGTH: 16
<212> TYPE: PRT
<213> ORGANISM: Glycine soja
<220> FEATURE:
<223> OTHER INFORMATION: DEDEDEDEDKPRPSRP

<400> SEQUENCE: 8

Asp Glu Asp Glu Asp Glu Asp Glu Asp Lys Pro Arg Pro Ser Arg Pro
1               5                   10                  15

<210> SEQ ID NO 9
<211> LENGTH: 14
<212> TYPE: PRT
<213> ORGANISM: Glycine soja
<220> FEATURE:
<223> OTHER INFORMATION: DEDEDEDKPRPSRP

<400> SEQUENCE: 9

Asp Glu Asp Glu Asp Glu Asp Lys Pro Arg Pro Ser Arg Pro
1               5                   10

<210> SEQ ID NO 10
<211> LENGTH: 15
<212> TYPE: PRT
<213> ORGANISM: Glycine soja
<220> FEATURE:
<223> OTHER INFORMATION: DEDEDKPRPSRPSQG

<400> SEQUENCE: 10

Asp Glu Asp Glu Asp Lys Pro Arg Pro Ser Arg Pro Ser Gln Gly
1               5                   10                  15

<210> SEQ ID NO 11
<211> LENGTH: 21
<212> TYPE: PRT
<213> ORGANISM: Glycine soja
<220> FEATURE:
<223> OTHER INFORMATION: GKREQDEDEDEDEDKPRPSRP

<400> SEQUENCE: 11

Gly Lys Arg Glu Gln Asp Glu Asp Glu Asp Glu Asp Glu Asp Lys Pro
1               5                   10                  15

Arg Pro Ser Arg Pro
            20

<210> SEQ ID NO 12
<211> LENGTH: 15
<212> TYPE: PRT
<213> ORGANISM: Glycine soja
<220> FEATURE:
<223> OTHER INFORMATION: HQQEEENEGGSILSG
```

```
<400> SEQUENCE: 12

His Gln Gln Glu Glu Glu Asn Glu Gly Gly Ser Ile Leu Ser Gly
1               5                   10                  15

<210> SEQ ID NO 13
<211> LENGTH: 16
<212> TYPE: PRT
<213> ORGANISM: Glycine soja
<220> FEATURE:
<223> OTHER INFORMATION: QGENEGEDKGAIVTVK

<400> SEQUENCE: 13

Gln Gly Glu Asn Glu Gly Glu Asp Lys Gly Ala Ile Val Thr Val Lys
1               5                   10                  15

<210> SEQ ID NO 14
<211> LENGTH: 9
<212> TYPE: PRT
<213> ORGANISM: Glycine soja
<220> FEATURE:
<223> OTHER INFORMATION: SVIKPPTDE

<400> SEQUENCE: 14

Ser Val Ile Lys Pro Pro Thr Asp Glu
1               5

<210> SEQ ID NO 15
<211> LENGTH: 7
<212> TYPE: PRT
<213> ORGANISM: Glycine soja
<220> FEATURE:
<223> OTHER INFORMATION: IKPPTDE

<400> SEQUENCE: 15

Ile Lys Pro Pro Thr Asp Glu
1               5

<210> SEQ ID NO 16
<211> LENGTH: 7
<212> TYPE: PRT
<213> ORGANISM: Glycine soja
<220> FEATURE:
<223> OTHER INFORMATION: NEGDVLV

<400> SEQUENCE: 16

Asn Glu Gly Asp Val Leu Val
1               5

<210> SEQ ID NO 17
<211> LENGTH: 10
<212> TYPE: PRT
<213> ORGANISM: Glycine soja
<220> FEATURE:
<223> OTHER INFORMATION: YNTGDEPVVA

<400> SEQUENCE: 17

Tyr Asn Thr Gly Asp Glu Pro Val Val Ala
1               5                   10

<210> SEQ ID NO 18
<211> LENGTH: 26
<212> TYPE: PRT
<213> ORGANISM: Glycine soja
<220> FEATURE:
<223> OTHER INFORMATION: HGKHEDDEDEDEEEDQPRPDHPPQRP

<400> SEQUENCE: 18
```

```
His Gly Lys His Glu Asp Asp Glu Asp Glu Asp Glu Glu Asp Gln
1               5                   10                  15

Pro Arg Pro Asp His Pro Pro Gln Arg Pro
            20                  25

<210> SEQ ID NO 19
<211> LENGTH: 25
<212> TYPE: PRT
<213> ORGANISM: Glycine soja
<220> FEATURE:
<223> OTHER INFORMATION: GKHEDDEDEDEEEDQPRPDHPPQRP

<400> SEQUENCE: 19

Gly Lys His Glu Asp Asp Glu Asp Glu Asp Glu Glu Asp Gln Pro
1               5                   10                  15

Arg Pro Asp His Pro Pro Gln Arg Pro
            20                  25

<210> SEQ ID NO 20
<211> LENGTH: 21
<212> TYPE: PRT
<213> ORGANISM: Glycine soja
<220> FEATURE:
<223> OTHER INFORMATION: DDEDEDEEEDQPRPDHPPQRP

<400> SEQUENCE: 20

Asp Asp Glu Asp Glu Asp Glu Glu Glu Asp Gln Pro Arg Pro Asp His
1               5                   10                  15

Pro Pro Gln Arg Pro
            20

<210> SEQ ID NO 21
<211> LENGTH: 23
<212> TYPE: PRT
<213> ORGANISM: Glycine soja
<220> FEATURE:
<223> OTHER INFORMATION: HEDDEDEDEEEDQPRPDHPPQRP

<400> SEQUENCE: 21

His Glu Asp Asp Glu Asp Glu Asp Glu Glu Asp Gln Pro Arg Pro
1               5                   10                  15

Asp His Pro Pro Gln Arg Pro
            20

<210> SEQ ID NO 22
<211> LENGTH: 7
<212> TYPE: PRT
<213> ORGANISM: Glycine soja
<220> FEATURE:
<223> OTHER INFORMATION: SGPLVNP

<400> SEQUENCE: 22

Ser Gly Pro Leu Val Asn Pro
1               5
```

FUNCTIONAL PEPTIDES FOR OBESITY DISORDERS

CROSS REFERENCE TO RELATED APPLICATIONS

Figure 1:
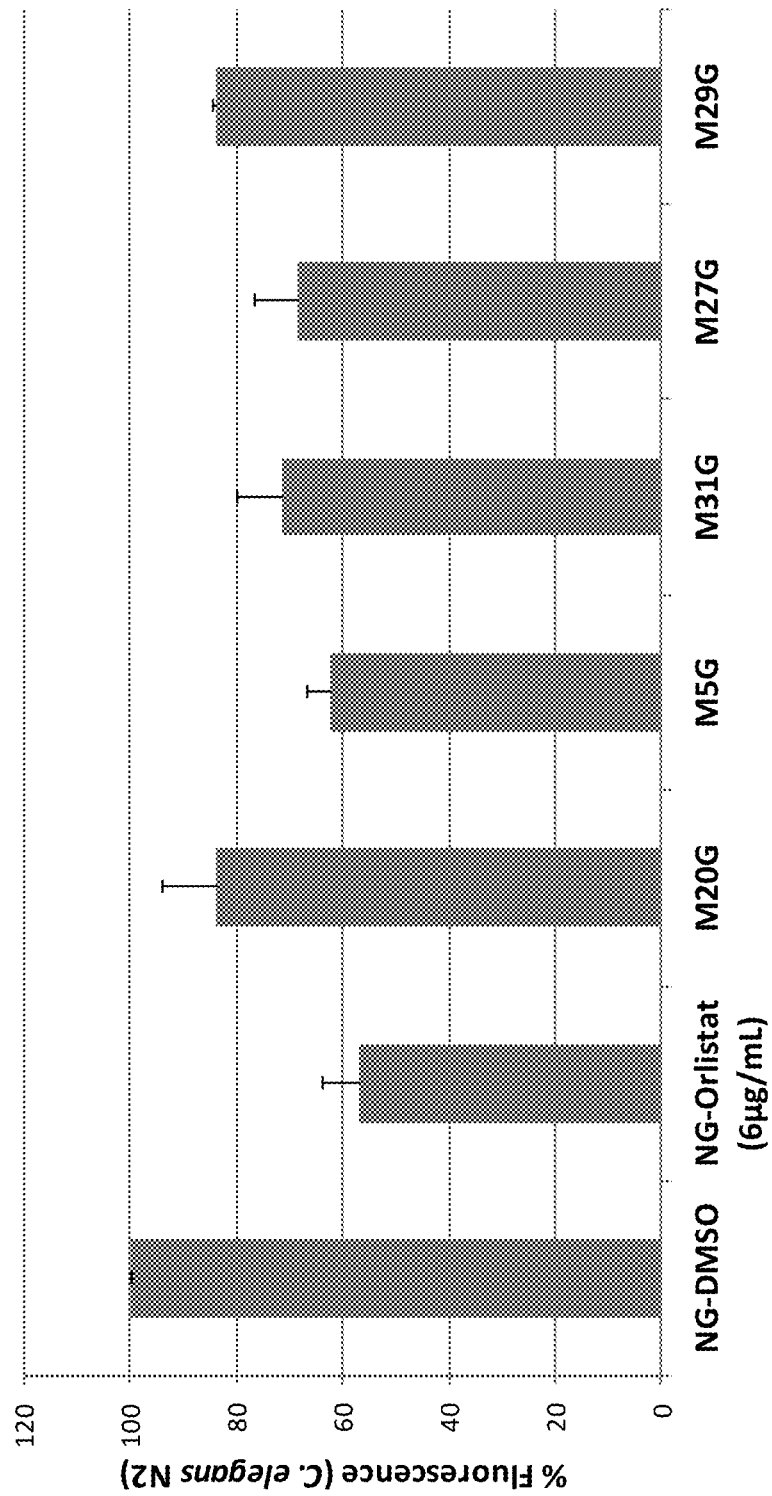

This application is a National Stage of International Application No. PCT/EP2013/053233, filed on Feb. 19, 2013, the contents of all of which are incorporated herein by reference in their entirety.

FIELD OF THE INVENTION

The present invention concerns certain peptides obtainable by hydrolysis from soy glycinin by the action of supernatant cultures of strains belonging to the genera *Lactobacillus* or *Streptococcus*.

These peptides, extracts containing them and food products containing them are useful for the treatment and/or prevention of obesity and oxidative stress.

BACKGROUND PRIOR ART

Obesity is a serious epidemic in our modern society leading to the development of multiple detrimental pathologies. Obesity related disorders can lead to multiple long-term complications such as type II diabetes, cardiovascular diseases, several types of cancer and many other maladies. It is clear that behavioral modifications in diet and energy expenditure can result in weight loss or be the cause of obesity when energy intake exceeds energy expenditure. Much focus has been given to potential pharmaceutical treatment against obesity, especially new approaches are based on the search of functional compounds able to inhibit the digestion of dietary lipids (Shi Y, Burn P; 2004; Lipid metabolic enzymes: emerging drug targets for the treatment of obesity; Nat. Rev. Drug Discover. 3: 695-710).

In the last decades, a great number of enzymes involved in lipid metabolism have been purified and characterized. Lipases that digest fats, both triacylglycerol and phospholipids, are of major interest for obesity. One of the most important lipases is pancreatic lipase (PL) accounting for the hydrolysis of 50-70% of dietary fats (Mukherjee M; 2003; Human digestive and metabolic lipases: a brief review; J. Mol. Catal. Enzym. B 22: 369-376). In the search for antiobesity compounds, PL inhibition has been one of the most widely studied target mechanisms (Birari R B, Bhutani K K; 2007; Pancreatic lipase inhibitors from natural sources: unexplored potential; Drug Discover. Today 12: 879-889). To date, Orlistat, is the only drug accepted in Europe that reduces fat absorption by a peripheral mechanism of action (Lunder M, Bratkovic, T, Kreft, S and Strukelj, B; 2005; Peptide inhibitor of pancreatic lipase selected by phage display using different elution strategies; Journal of Lipid Research 46: 1512-1516).

Additionally, there are considerable evidences from cell and animal studies suggesting the importance of pancreatic phospholipase A2 (PLA2) in the digestion and absorption of lipids. The phospholipase A2 (PLA2) family catalyzes the hydrolysis of membrane phospholipids, releasing arachidonic acid (AA), docosahaxaenoic acid (DHA), and other polyunsaturated fatty acids (PUFAs). The released PUFAs are precursors of a variety of eicosanoids, 20 carbon compounds that include prostaglandins, thromboxanes, leukotrienes, and lipoxins responsable of inflammatory reactions. It has been demonstrated that PLA2 and its downstream products can act as important biological mediators in adipose tissue, activation of PLA2 by several cytokines suggests that this enzyme function as cellular links between inflammatory pathways and lipid metabolism thereby constituting a key target in obesity (Abbott M, Tang T mad Sul H; 2010; The role of phospholipase A2-derived mediators in obesity; Drug Discovery Today: Disease Mechanisms 7:3-4).

On the other hand, most of the genes encoding enzymes of lipid metabolism have been cloned and sequenced from different organisms, including humans. Phylogenetic studies have revealed that lipid metabolism is a very well conserved pathway from yeast to humans opening the way to the use of model organisms in the study of antiobesity drugs. In this sense, the nematode *Caenorhabditis elegans* is a perfect model organism for the study of obesity (Chiang S H, MacDougald O A; 2003; Will fatty worms help cure human obesity; Trends Genet. 19: 523-525). In fact, analysis in *C. elegans* of fat reducing gene inactivation using interference RNA have identify 305 genes related with reduced body fat and 112 genes involved in increased fat storage, many of them with mammalian homologues (Ashrafi K et al.; 2003; Genome-wide RNAi analysis of *Caenorhabditis elegans* fat regulatory genes; Nature 421: 268-272). Also in *C. elegans*, lipases are key factors in obesity. Recent reports of groups working on lipases of *C. elegans* indicate that in this organism fat metabolism is an unexpected link between obesity, reproduction and aging (Wang M C et al.; 2008; Fat metabolism links germline stem cells and longevity in *C. elegans*; Science 232: 957-960; Xie T; 2008; Burn fat, live longer; Science 232: 865-866).

Natural compounds potentially preventing the development of obesity and related metabolic disorders have been studied. Gargouri and coworkers reported that some soybean proteins have an inhibitory effect on pancreatic lipase (Gragouri et al; 1984; Studies on the inhibition of pancreatic and microbial lipases by soybean proteins; J Lipid Res., 25:1214-1221). These molecules do not have a direct effect in the enzyme; they modify the lipid emulsions, avoiding the contact between the enzyme and the substrate. In the same way, several authors have explained the presence of basic proteins in some seed with inhibitory properties of lipase activity and later Miyazaki et al., in the U.S. Pat. No. 5,411,956 described some proteins used as inhibitors of lipase in the treatment of obesity (Wang and Huang; 1984; Inhibitors of lipase activities in soybean and other oil seeds; Plant Physiol., 76:929-934; Tani et al; 1994; Purification and characterization of proteinous inhibitor of lipase from wheat flour; J Agri Food Chem., 42:2382-2385; Tsujita et al; 1996; Studies of the inhibition of pancreatic and carboxylester lipases by protamine; J Lipid Res., 37:1481-1487; Gragouri et al; 1984; Inhibition of pancreatic and microbial lipases by proteins; Biochim. Biophys. Acta., 795:326-331).

In the same manner, these and other authors proved that the intestinal lipid absorption was reduced by phenolic substances (i.e., chlorogenic acid, (+) catechin, epicatechin, phloridzin, rutin and procyanidins (condensed tannins)) causing an in vitro inhibitory effect on digestive lipases (Wang et al; 2006; Green tea catechins inhibit pancreatic phospholipase A2 and intestinal absorption of lipids in ovariectomized rats; J Nutr Bioch., 17:492-498), Juhel et al (Juhel et al; 2000; Green tea extract (AR25) inhibits lipolysis of triglycerides in gastric and duodenal medium in vitro; J Nutr. Biochem., 11:45-51), Sugiyama et al (Sugiyama et al; 2007; Oligomeric Procyanidins in Apple Polyphenol Are Main Active Components for Inhibition of Pancreatic Lipase and Triglyceride Absorption; J Agric Food Chem., 55:4604-4609) and Rahul et al (Rahul et al; 2007; Pancreatic lipase inhibitors from natural sources: unexplored potential "Drug Discovery" today., 12:19-20).

However, the study of functional peptides related with obesity, obtained chemically, biotechnologically or by means of enzymatic treatment from proteins, remains an area to explore, although is raising increasing interest. The present invention is focused on functional peptides useful in the treatment of obesity and oxidative stress obtained from microbial digestion of glycinin by using lactic acid bacteria strains.

SUMMARY OF THE INVENTION

Accordingly in a first aspect, the invention relates to peptides with PL (pancreatic lipase) and/or PLA2 (pancreatic phospholipase) inhibiting activities obtainable by hydrolysis from soy glycinin.

In a preferred aspect, the invention relates to a peptide having PL (pancreatic lipase) and/or PLA2 (phospholipase A2) inhibiting activity obtained by hydrolysis of soy glycinin with *Streptococcus thermophilus* CNCM 1-2776 and/or *Streptococcus thermophilus* CNCM 1-1630 and/or *Lactobacillus paracasei* subsp *paracasei* CNCM I-4270 for use in the treatment or prevention of obesity and/or oxidative stress.

In a second aspect, the invention relates to peptides with PL and/or PLA2 inhibiting activities, selected from the group consisting of: SEQ ID No. 1: EEEGGSVLSG, SEQ ID No. 2: SDNFEY, SEQ ID No. 3: EEDQPRPDHPPQRP, SEQ ID No. 4: SVIKPPTD, SEQ ID No. 5: QGENEEEDSGAIVTVK, SEQ ID No. 6: QGENEGEDKGAIVT, SEQ ID No. 7: QDEDEDEDEDKPRPSRP, SEQ ID No. 8: DEDEDEDEDKPRPSRP, SEQ ID No. 9: DEDEDEDKPRPSRP, SEQ ID No. 10: DEDEDKPRPSRPSQG, SEQ ID No. 11: GKREQDEDEDEDEDKPRPSRP, SEQ ID No. 12: HQQEEENEGGSILSG, SEQ ID No. 13: QGENEGEDKGAIVTVK, SEQ ID No. 14: SVIKPPTDE, SEQ ID No. 15: IKPPTDE, SEQ ID No. 16: NEGDVLV, SEQ ID No. 17: YNTGDEPVVA, SEQ ID No. 18: HGKHEDDEDEDEEEDQPRPDHPPQRP, SEQ ID No. 19: GKHEDDEDEDEEEDQPRPDHPPQRP, SEQ ID No. 20: DDEDEDEEEDQPRPDHPPQRP, SEQ ID No. 21: HEDDEDEDEEEDQPRPDHPPQRP, and SEQ ID No. 22: SGPLVNP.

In a preferred aspect the peptides are selected from the group consisting of SEQ ID No. 1: EEEGGSVLSG, SEQ ID No. 2: SDNFEY, SEQ ID No. 3: EEDQPRPDHPPQRP, SEQ ID No. 4: SVIKPPTD, SEQ ID No. 5: QGENEEEDSGAIVTVK and SEQ ID No. 6: QGENEGEDKGAIVT, which either in isolated form and/or in the form of an extract may be used for the treatment and/or prevention of an obesity disorder as well as against an oxidative stress.

In a third aspect, the invention relates to a food product which comprises at least one of the peptides with PL (pancreatic lipase) and/or PLA2 (pancreatic phospholipase) inhibiting activities, selected from the group consisting of: SEQ ID No. 1: EEEGGSVLSG, SEQ ID No. 2: SDNFEY, SEQ ID No. 3: EEDQPRPDHPPQRP, SEQ ID No. 4: SVIKPPTD, SEQ ID No. 5: QGENEEEDSGAIVTVK and SEQ ID No. 6: QGENEGEDKGAIVT, or an extract comprising at least one of the mentioned peptides useful for the treatment and/or prevention of obesity and oxidative stress.

In a fourth aspect, the invention relates to a pharmaceutical composition which comprises at least one of the peptides with PL (pancreatic lipase) and/or PLA2 (pancreatic phospholipase) inhibiting activities, selected from the group consisting of: SEQ ID No. 1: EEEGGSVLSG, SEQ ID No. 2: SDNFEY, SEQ ID No. 3: EEDQPRPDHPPQRP, SEQ ID No. 4: SVIKPPTD, SEQ ID No. 5: QGENEEEDSGAIVTVK and SEQ ID No. 6: QGENEGEDKGAIVT, or an extract comprising at least one of the mentioned peptides useful for the treatment and/or prevention of obesity and oxidative stress.

In a further aspect, the invention relates to the use of certain bacteria from the genus *Lactobacillus* and *Streptococcus*, in particular, *Streptococcus thermophilus* CNCM 1-2776, *Streptococcus thermophilus* CNCM 1-1630 and *Lactobacillus paracasei* CNCM 1-4270, supernatants or cells containing the proteases of the said strains for obtaining the peptides and or extracts containing the peptides with PL (pancreatic lipase) and/or PLA2 (pancreatic phospholipase) inhibiting activities, selected from the group consisting of: SEQ ID No. 1: EEEGGSVLSG, SEQ ID No. 2: SDNFEY, SEQ ID No. 3: EEDQPRPDHPPQRP, SEQ ID No. 4: SVIKPPTD, SEQ ID No. 5: QGENEEEDSGAIVTVK and SEQ ID No. 6: QGENEGEDKGAIVT.

FIGURES

Figure 2:
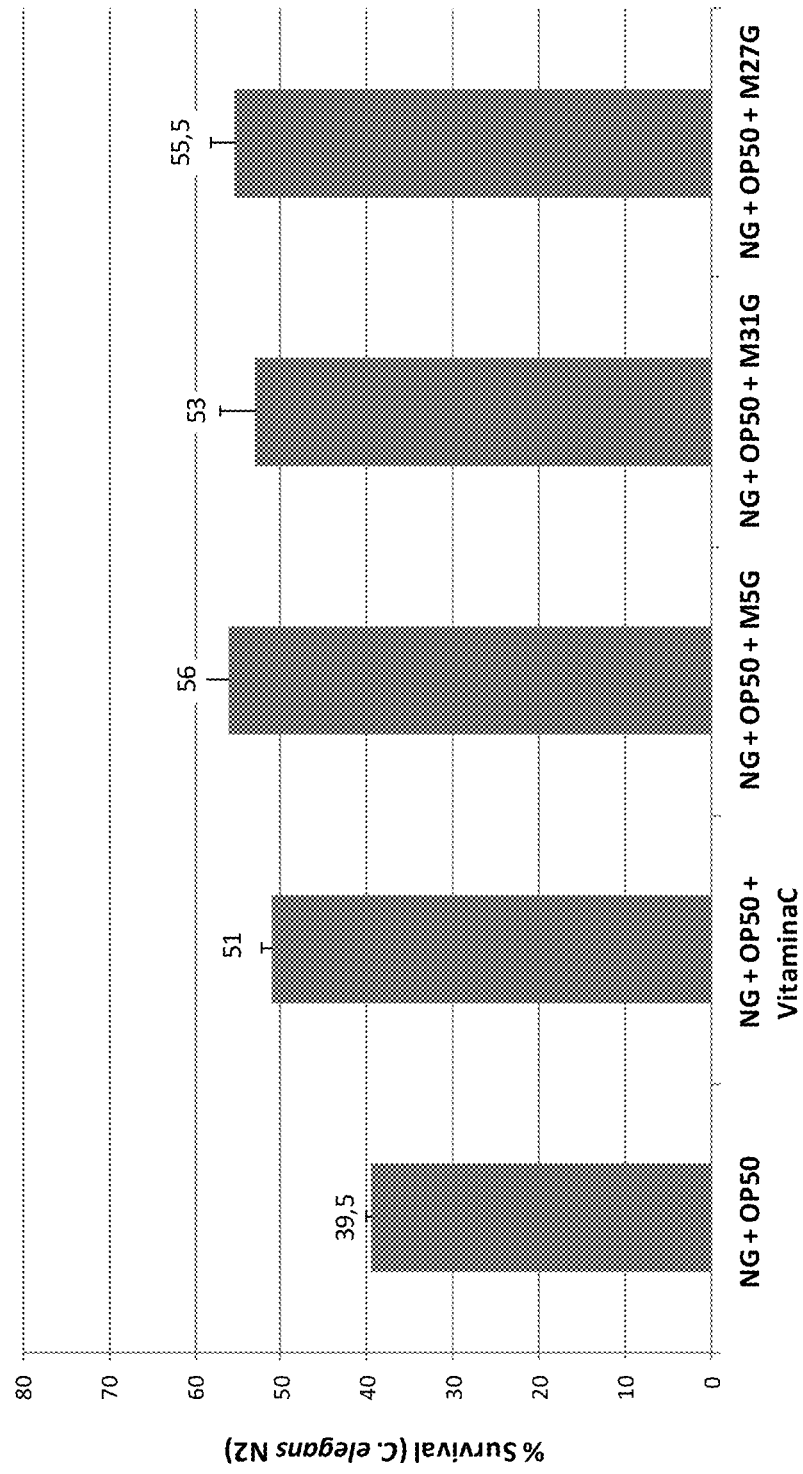

FIG. 1 represents the effect on *C. elegans* body fat reduction of peptide extracts obtained from soy glycinin and selected from PLA2 inhibition assay FIG. 2 represents the effect of protection against an acute oxidative stress by different peptide extracts in *C. elegans*

DETAILED DESCRIPTION OF THE INVENTION

The present invention provides different glycinin peptides obtained by hydrolysis with different strains of lactic acid bacteria for use in treatment and/or prevention of obesity disorder and oxidative stress. These peptides are able to in vitro inhibit lypolitic enzymes (PL and PLA2) and reduce fat accumulation and protect against acute oxidative stress in an in vivo model using *Caenorhabditis elegans*.

In vitro studies were carried out in order to select several strains of lactic acid bacteria able to release peptides from soy glycinin able to inhibit enzymatic activities of relevance in obesity disorders. Peptide extracts were obtained after 72 h of hydrolysis of soy glycinin by supernatant cultures of ten different strains belonging to the genera *Lactobacillus* or *Streptococcus*. The generated extracts were screened for their capacity to in vitro inhibit PL and PLA2 enzymes. Finally, the selected peptide extracts were then screened for their ability to reduce fat accumulation using an in vivo model of *Caenorhabditis elegans*, and subsequently the selected peptide extracts were also tested for their ability to protect against an acute oxidative stress using the same animal system.

As a result of this study, it was found that peptide extracts obtained after hydrolysis of glycinin with proteases from supernatant of some strains were able to in vitro inhibit PL and PLA2, and to reduce fat accumulation and protect against oxidative stress using the in vivo model of *C. elegans*. The antioxidant peptides responsible for the in vitro PL and PLA2 inhibition and fat reduction in vivo were then identified.

Consumption of these specific peptide extracts can be advantageously used in persons suffering obesity or in persons at risk of suffering obesity, such as people with a family history of obesity or people with problems in lipid metabolism.

Selection of Strains

For the purpose of selecting the most efficient lactic acid bacteria having protease activity against glycinin, different strains of the genera *Lactobacillus* and *Streptococcus* were subject to the following hydrolysis assay.

The substrate selected to carry out the process of hydrolysis was soy glycinin. Glycinin is the soy major protein extracted from soy flour after treatment with mercaptoethanol followed by two centrifugation steps as described in Thanh V. H. et al. (Major proteins of soybean seeds: a straightforward fractionation and their characterization. 1976. J Agric Food Chem 24: 1117-1121). Among the enzymatic sources used to degrade glycinin, ten strains were tested: 6 strains from *Streptococcus* genera (strains 2, 3, 4, 5, 6, 7) and 4 strains from *Lactobacillus* genera (strains 8, 9, 10 and 11). All these strains were grown in optimal medium (MRS for *Lactobacillus* strains and BHI for *Streptococcus* strains) during 17 h at 37° C. and the proteases with a molecular weight above 10 KDa both in supernatant and cells were concentrated to be used as enzymatic sources in glycinin hydrolysis assays. On one hand, proteases from the supernatant were obtained after centrifugation for 15 min at 4000 rpm. Then the supernatant was ultrafiltrated by 10 KDa and the top was resuspended in 2 ml with 50 mM citrate phosphate buffer pH 7. On the other hand, cells obtained from the different cultures were washed with saline solution for 15 min at 4000 rpm and resuspended in 50 mM citrate phosphate buffer pH 7 to evaluate the protease activity in cells and supernatant (Table 1).

TABLE 1

Protease activity from different culture collection LAB strains.

| Strains | Microorganisms | Protease activity (U.I./ml) | |
|---|---|---|---|
| | | Supernatant | cell |
| 2 | *Streptococcus thermophilus* CNCM I-2965 | 0.005 | 0.003 |
| 3 | *Streptococcus thermophilus* CNCM I-2785 | 0.009 | 0.001 |
| 4 | *Streptococcus thermophilus* CNCM I-4269 | 0.001 | 0.002 |
| 5 | *Streptococcus thermophilus* CNCM I-3211 | 0.003 | 0.001 |
| 6 | *Streptococcus thermophilus* CNCM I-2776 | 0.006 | 0.001 |
| 7 | *Streptococcus thermophilus* CNCM I-1630 | 0.003 | 0.001 |
| 8 | *Lactobacillus delbrueckii lactis* CNCM I-4280 | 0.028 | 0.009 |
| 9 | *Lactobacillus helveticus* CNCM I-4279 | 0.010 | 0.012 |
| 10 | *Lactobacillus paracasei paracasei* CNCM I-4270 | 0.016 | 0.005 |
| 11 | *Lactobacillus paracasei paracasei* CNCM I-1518 | 0.029 | 0.006 |

From the above it was seen that the culture supernatant of lactic acid bacteria strains were found to be most efficient in providing the highest protease activity and therefore producing functional peptides in obesity.

Obtention of Peptide Extracts

Enzymatic hydrolysis was carried out for 72 h at 37° C. with 13.5 ml of 1% of glycinin in 50 mM citrate phosphate buffer pH 7 and 1.5 ml of each 10 KDa concentrated culture supernatant under study. The reaction was stopped by ultrafiltration with 3 KDa filters and the lower fractions, containing peptides released after hydrolysis were in vitro evaluated for testing their ability to inhibit lipolytic enzymes as PL and PLA2 and studying their in vivo capacity to reduce fat accumulation in a *C. elegans* model.

Screening of Peptide Extracts for their Capacity to Inhibit In Vitro PL and PLA2 Enzyme Activity Inhibition of PL was determined using 4-methyl umbelliferyl oleate (4MUO) as substrate as described by Sugiyama et al. (Oligomeric procyanidins in apple polyphenol are main active components for inhibition of pancreatic lipase and triglyceride absorption. J Agric Food Chem (2007); 55: 4604-4609) with some modifications. Aliquots of 25 μl of each peptide extract were incubated with 25 μl of PL solution (1 mg/ml) and preincubated for 10 minutes at 26° C. with stirring of 500 rpm. Reaction was initiated by adding 50 μl of 4MUO (0.1 mM) dissolved in Dulbecco's buffer. After incubation at 26° C. for 20 minutes with constant stirring (500 rpm) the reaction was stopped by adding 100 μl of 0.1 M sodium citrate buffer (pH 4.2). The amount of 4-methyl umbelliferone released by the enzyme was determined by fluorescence. Peptide extracts were used as inhibitors in the enzymatic assay but had to be diluted 1/20 or 1/50 because of the interference between the fluorescence and the buffer containing the peptides.

Inhibition of PLA2 enzyme was determined by High Performance Liquid Chromatography (HPLC) using 1,2-dioleoyl-sn-glycero-3-phosphocholine (DOPC) as substrate as described by Singh et al. (A rapid isocratic high-performance liquid chromatography method for determination of cholesterol and 1,2-dioleoyl-sn-glycero-3-phosphocholine. Journal of Chromatography (2005); 1073:347-353). Waters 2695 HPLC with Waters 2996 Photodiode detector Array and a C8 column Hypersil BDS (250×4.6 mm, 5 uM) were used carrying out an eluent isocratic method formed by a mixture of ammonium phosphate buffer 50 mM pH 2.7: methanol (15:85, v/v). Table 2 contains PL inhibition values by the peptide extracts obtained from soy glycinin. Table 3 contains PLA2 inhibition values by the peptide extracts obtained from soy glycinin.

TABLE 2

Percentage of PL inhibition by peptide extracts from soy glycinin with supernatants and cells from the analyzed strains.

| | % Inhibition PL - Glycinin Peptides extracts D(1/20) | |
|---|---|---|
| Glycinin control 72 h | 2.4 ± 4.6 | |
| Strains | Supernatants | Cells |
| 2 - *St. thermophilus* | 3.0 ± 4.5 | 2.0 ± 4.9 |
| 3 - *St. thermophilus* | 4.5 ± 5.6 | 1.5 ± 5.4 |
| 4 - *St. thermophilus* | 0.7 ± 3.3 | 1.6 ± 4.0 |
| 5 - *St. thermophilus* | 2.4 ± 5.0 | 1.1 ± 2.4 |
| 6 - *St. thermophilus* | 0.9 ± 3.9 | 3.7 ± 3.2 |
| 7 - *St. thermophilus* | 2.0 ± 5.6 | 5.7 ± 1.9 |
| 8 - *L. helveticus* | 1.3 ± 2.7 | 4.3 ± 3.4 |
| 9 - *L. acidophilus* | 3.4 ± 3.3 | 2.1 ± 3.5 |
| 10 - *L. paracasei* subsp *paracasei* | 2.6 ± 3.3 | 3.3 ± 3.1 |
| 11 - *L. paracasei* subsp *paracasei* | 3.1 ± 5.3 | 4.5 ± 6.2 |

TABLE 3

Percentage of PLA2 inhibition by peptide extracts from soy glycinin with supernatants and cells from the analyzed strains.

| Glycinin control 72 h | % Inhibition PLA2 - Glycinin Peptide extracts 9.5 ± 7.4 | |
|---|---|---|
| Strains | Supernatants | Cells |
| 2 - St. thermophilus | 6.4 ± 3.2 | 7.4 ± 1.9 |
| 3 - St. thermophilus | 2.8 ± 0.7 | 19.2 ± 1.3 |
| 4 - St. thermophilus | 4.9 ± 0.3 | 8.6 ± 2.4 |
| 5 - St. thermophilus | 5.3 ± 1.7 | 11.0 ± 2.9 |
| 6 - St. thermophilus | 17.1 ± 2.3 | 13.0 ± 3.9 |
| 7 - St. thermophilus | 21.5 ± 1.7 | 6.7 ± 4.0 |
| 8 - L. helveticus | 7.9 ± 0.5 | 3.5 ± 1.1 |
| 9 - L. acidophilus | 9.0 ± 2.6 | 5.7 ± 3.2 |
| 10 - L. paracasei subsp paracasei | 20.9 ± 1.6 | 7.8 ± 1.0 |
| 11 - L. paracasei subsp paracasei | 14.0 ± 3.0 | 3.5 ± 0.9 |

The best inhibitory peptide extracts from soy glycinin were selected to be tested in vivo with C. elegans model. These peptide extracts and their assigned codes are summarized in Table 4.

TABLE 4

Group of the selected peptide extracts for in vivo analysis

| Samples selected from PLA2 inhibition assay | Sample Code | % PLA2 inhibition |
|---|---|---|
| St. thermophilus 3 cells Glycinin 72 h | M20G | 19.2 ± 1.3 |
| St. thermophilus 6 supernatant Glycinin 72 h | M5G | 17.1 ± 2.3 |
| St. thermophilus 7 supernatant Glycinin 72 h | M31G | 21.5 ± 1.7 |
| L. paracasei subsp paracasei 10 supernatant Glycinin 72 h | M27G | 20.9 ± 1.6 |
| L. paracasei subsp paracasei 11 supernatant Glycinin 72 h | M29G | 14 ± 3 |

Screening of Peptide Extracts for their Ability to In Vivo Reduce Fat Accumulation The ability to reduce body fat content in the nematode C. elegans was analyzed in a group of 5 peptide extracts previously obtained from glycinin (see Table 4). These samples were selected by their high effect on PL and PLA2 in vitro inhibition. Specifically, 5 peptide extracts were selected from the PLA2 inhibition assay (M20G, M5G, M31G, M27G and M29G). Body fat content was analyzed in the C. elegans wild type strain N2 by Red Nile dying of living nematodes. Experiments were carried out with age-synchronized populations, starting from egg-stage to young adult stage (3-day adults). During the experiments, worms were cultured in the NGM agar plates as control condition, NGM with the corresponding peptide extracts (100 μL/plate) and NGM with 6 μg/mL of Orlistat as positive control. Nile Red was added on top of the NG plates already seeded with Escherichia coli OP50 strain to a final concentration of 0.05 μg/ml. After incubation at 20° C., young adult worms (60 worms per condition) were taken to measure the in vivo fluorescence in a VersaFluor™ Fluorometer System. Fluorescence obtained in treated worms was calculated from fluorescence of worms fed in control conditions (reference sample). Experiments were carried out by duplicate.

The overall results obtained in the evaluation of the 5 peptide extracts showed a higher effect on body fat reduction in the case of those with PLA2 inhibitory capacity (Table 5 and FIG. 1).

Peptide extracts selected from their PLA2 inhibitory effect were, in general, more effective upon lipid reduction in C. elegans (Table 5). The percentage of fluorescence reduction, as shown in FIG. 1, were from 16.2 to 37.7%. It is important to highlight the effect of MSG, M27G and M31G with 37.7%, 31.6% and 28.6% of fluorescence reduction respectively.

To summarize, it has been found that a group of peptide extracts with a significant in vitro inhibitory effect on PLA2 have also an important in vivo effect on body fat reduction.

TABLE 5

Percentage of C. elegans body fat reduction produced by peptide extracts selected from the previous enzyme inhibition assay.

| Samples selected from PLA2 inhibition assay | Sample Code | % Fat reduction (C. elegans) |
|---|---|---|
| St. thermophilus 3 cells Glycinin 72 h | M20G | 16.05 |
| St. thermophilus 6 supernatant Glycinin 72 h | M5G | 37.71 |
| St. thermophilus 7 supernatant Glycinin 72 h | M31G | 28.57 |
| L. paracasei subsp paracasei 10 supernatant Glycinin 72 h | M27G | 31.61 |
| L. paracasei subsp paracasei 11 supernatant Glycinin 72 h | M29G | 16.29 |

Screening of Peptide Extracts for their Capacity to Protect Against Acute Oxidative Stress The protection of the selected 5 peptide extracts against an acute oxidative stress was analyzed in the in vivo model of C. elegans.

Experiments were carried out with age-synchronized populations of C. elegans wild type strain N2. The nematodes were fed from egg stage to 5-day adult stage with the different peptide extracts (100 μL/plate). A control fed condition (NGM) and positive control (vitamin C, 0.1 μg/mL) were included. After incubation at 20° C., worms were submitted to an oxidative stress by transferring them to new plates with $H_2O_2$ (2 mM). Viability of worm population was determined after 5 h of incubation in each culture condition. Experiments were carried out by duplicate.

The 5 selected peptide extracts were analyzed in two different trials. The first one (see FIG. 2) included the samples which produced the highest in vitro inhibition of PLA2 (they reduce body fat in vivo between 28.6 and 39.1%). Samples M5G, M31G, M27G were obtained from glycinin substrates and all of them showed a high protection against oxidative stress in the nematode. We observed high percentages of survival after oxidative stress (between 53 and 64%) compared with control conditions (39.5%). The results show high protection against oxidative stress and ability to reduce fat content in the nematode for peptide extracts M5G, M31G y M27G. (FIG. 2).

In summary, a group of 3 peptide extracts, M5G, M31G, M27G, obtained from glycinin by hydrolysis with strains St. thermophilus 6, L. paracasei subsp paracasei 10 and St. thermophilus 7, have a high effect on fat reduction and a significant protection against oxidative stress in the in vivo model of C. elegans, demonstrating their beneficial effect on both functionalities (Table 6).

TABLE 6

Protection against oxidative stress of peptide extracts selected from PLA2 assay.

| Samples selected from PLA2 assay | Sample Code | % Fat reduction (C. elegans) | % Survival (C. elegans) |
|---|---|---|---|
| St. thermophilus 6 supernatant Glycinin 72 h | M5G | 37.71 | 56 |
| St. thermophilus 7 supernatant Glycinin 72 h | M31G | 28.57 | 53 |
| L. paracasei subsp paracasei 10 supernatant Glycinin 72 h | M27G | 31.61 | 55.5 |

The following strains were then preferably selected for the purpose of the present invention.

Strain 6: *Streptococcus thermophilus* CNCM I-2776
Strain 7: *Streptococcus thermophilus* CNCM I-1630
Strain 10: *Lactobacillus paracasei* subsp *paracasei* CNCM I-4270

The present invention also encompasses the use of above mentioned strains, but also mutants strains or genetically transformed strains derived from any one of the parent strains still having protease activity against glycinin and producing the functional peptides of the present invention. These mutant or genetically transformed strains can be strains wherein one or more endogenous gene(s) of the parent strain has (have) been mutated, for instance to modify some of its metabolic properties. They can also be strains resulting from the genetic transformation of the parent strain by one or more gene/s of interest, for instance in order to give to said strains additional physiological features.

Identification of Functional Peptides with Capacity to In Vitro Inhibit PLA2, Reduce Fat and Protect Against Oxidative Stress in *C. elegans* Model The 3 peptide extracts able to in vitro inhibit PLA2, reduce fat and protect against oxidative stress in vivo were selected to identify the functional peptide sequence present on them. The identification of functional peptides was carried out with samples, M5G, M27G and M31G and obtained by nESI-MS/MS.

Table 7 contains the peptides sequences identified from glycinin and the number of occurrences in each evaluated sample. All the peptides showed in Table 7 only were present in samples treated with strains *St. thermophilus* 6 and 7 and *Lactobacillus paracasei* subsp *paracasei* 10, and are not identified in the control samples without hydrolytic treatment.

TABLE 7

Frequency peptide sequences from soy glycinin identified in M5G, M27G and M31G samples.

| Sequence | Molecular weight | M5G | M27G | M31G |
|---|---|---|---|---|
| V.AVSLIDTN.S | 831.53 | 1 | | |
| Y.LAGNQEQEFLK.Y | 1276.07 | 2 | | |
| Y.LAGNQEQEFLQ.Y | 1276.07 | 1 | | |
| L.AGNQEQEFLK.Y | 1162.99 | 2 | | 2 |
| L.AGNQEQEFLQ.Y | 1162.99 | 1 | | |
| Q.GENEGEDKGAIVT.V | 1317.85 | 1 | | |
| Q.GENEEEDSGAIVTVKGG.L | 1690.05 | 1 | | |
| N.EGEDKGAIVTVKG.G | 1301.91 | 1 | | |
| N.EGEDKGAIVTVKGG.L | 1358.95 | 1 | | |
| N.EEEDSGAIVTVKGG.L | 1389.95 | 1 | | |
| E.EEDSGAIVTVKGG.L | 1260.95 | 1 | | |
| E.EDSGAIVTVKGG.L | 1131.89 | 1 | | |
| V.TAPAMRKPQQEEDDDDEEEQP.Q | 2456.41 | 1 | | |
| V.TAPAMRKPQQEEDDDDEEEQPQ.C | 2585.41 | 1 | | 1 |
| E.EEEKGAIVTVK.G | 1201.93 | 1 | | |
| T.FEEPQQPQ.Q | 1001.89 | 1 | | |
| T.FEEPQQPQQRGQ.S | 1470.95 | 1 | | 1 |
| N.ALEPDHRVES.E | 1151.93 | 1 | | |
| R.HFNEGDVL.V | 928.7 | 1 | | |
| E.EEEEGGSVLSGFSK.H | 1452.97 | 1 | | |
| R.EQDEDEDEDEDKPRPSRPSQGK.R | 2585.41 | 1 | 1 | 1 |
| E.QDEDEDEDEDKPRPSRPSQGK.R | 2456.41 | 1 | | |
| E.QDEDEDEDEDKPRPSRPSQGKR.N | 2612.53 | 1 | | |
| D.EDEDEDEDKPRPSRPSQG.K | 2084.41 | 1 | | |
| D.EDEDEDEDKPRPSRPSQGK.R | 2213.44 | 1 | | |
| D.EDEDEDEDKPRPSRPSQGKR.N | 2369.53 | 1 | | |
| E.EDSGAIVTVK.G | 1017.91 | | 1 | |
| V.FDGEL.Q | 579.44 | | 3 | |
| E.GGLIQTW.N | 774.02 | | 1 | |
| D.EDDEDEQIPS.H | 1175.77 | | 1 | |
| E.DEQIPSHPPRRP.S | 1428.37 | | 1 | |
| K.REQDEDEDEDEDKPRPSRP.S | 2341.48 | | 2 | |
| K.REQDEDEDEDEDKPRPSRPS.Q | 2428.57 | | 2 | |
| K.REQDEDEDEDEDKPRPSRPSQGK.R | 2741.53 | | 2 | 1 |
| R.EQDEDEDEDEDKPRPSRP.S | 2185.42 | | 1 | |
| R.EQDEDEDEDEDKPRPSRPS.Q | 2272.48 | | 1 | |
| R.EQDEDEDEDEDKPRPSRPSQG.K | 2457.49 | | 1 | |
| E.DEDEDEDKPRPSRPSQGK.R | 2084.5 | | 1 | |
| K.HEDDEDEDEEEDQPRPDHPPQRP.S | 2810.5 | | 1 | |
| K.HEDDEDEDEEEDQPRPDHPPQRPS.R | 2897.56 | | 1 | |
| E.DDEDEEEDQPRPDHPPQRP.S | 2544.58 | | 1 | |
| E.DEDEEEDQPRPDHPPQRP.S | 2185.42 | | 1 | |
| E.DEDEEEDQPRPDHPPQRPS.R | 2272.42 | | 1 | |
| D.EDEEEDQPRPDHPPQRP.S | 2070.46 | | 1 | |

TABLE 7-continued

Frequency peptide sequences from soy glycinin identified in M5G, M27G and M31G samples.

| Sequence | Molecular weight | M5G | M27G | M31G |
|---|---|---|---|---|
| D.EEEDQPRPDHPPQRP.S | 1826.11 | 3 | | |
| D.EEEDQPRPDHPPQRPS.R | 1913.29 | 1 | | |
| E.EEDQPRPDHPPQRP.S | 1697.2 | 1 | | |
| E.DQPRPDHPPQRP.S | 1439.01 | 3 | | |
| T.FEEPQQPQQR.G | 1284.97 | | 1 | |
| G.DLIAVP.T | 626.51 | | 2 | |
| K.HQQEEENEGGSIL.S | 1469.11 | | 1 | |
| K.NLQGENEGEDKGAIVT.V | 1673.19 | | 1 | |
| K.NLQGENEGEDKGAIVTVK.G | 1900.41 | | 2 | |
| K.GKQQEEENEGSNIL.S | 1573.15 | | 1 | |
| K.GKQQEEENEGSNILS.G | 1661.13 | | 1 | |
| L.QGENEEEDSGAIVTVK.G | 1704.17 | | 1 | |
| K.REQDEDEDED.E | 1278.53 | | 1 | |
| K.REQDEDEDEDEDKPRPSRPSQ.G | 2556.64 | | 1 | |
| K.REQDEDEDEDEDKPRPSRPSQG.K | 2613.61 | | 1 | |
| K.REQDEDEDEDEDKPRPSRPSQGKR.N | 2898.01 | | 1 | |

Hydrolyzates M5G and M27G from strains *St. thermophilus* 6 and *Lactobacillus paracasei* subsp *paracasei* 10 were chosen and further purified by Reverse Phase Cromatography in order to identify the peptides responsible of in vivo fat reduction. Reverse Phase Cromatography fractions were assayed towards *C. elegans* to study fat reduction and identify peptides present in the positives ones from strains *St. thermophilus* 6 and *L. paracasei* subsp *paracasei* 10. (Table 8).

TABLE 8

Peptide sequences from soy glycinin identified in purified fractions from strains *St. thermophilus* 6 (M5G) and *L. paracasei* subsp *paracasei* 10 (M27G)

| SEQ ID No. | Peptide Sequence | Molecular weight(Da) | Fraction 6 strain 6 | Fraction 7 strain 6 | Fraction 6 strain 10 | Protein |
|---|---|---|---|---|---|---|
| 7 | QDEDEDEDEDKPRPSRP | 2055.88 | 4 | | 4 | Glycinin G4 |
| 8 | DEDEDEDEDKPRPSRP | 1927.99 | 1 | | | |
| 9 | DEDEDEDKPRPSRP | 1683.73 | 4 | | 8 | |
| 10 | DEDEDKPRPSRPSQG | 1711.87 | 1 | | | |
| 1 | EEEGGSVLSG | 1091.73 | | | 1 | |
| 11 | GKREQDEDEDEDEDKPRPSRP | 2525.89 | | | 8 | |
| 12 | HQQEEENEGGSILSG | 1612.89 | | 1 | | Glycinin G1 |
| 6 | QGENEGEDKGAIVT | 1445.89 | | 1 | | |
| 13 | QGENEGEDKGAIVTVK | 1672.91 | | 1 | | |
| 4 | SVIKPPTD | 855.46 | | 1 | | |
| 14 | SVIKPPTDE | 984.52 | | 1 | | |
| 15 | IKPPTDE | 798.49 | | 1 | | |
| 2 | SDNFEY | 773.75 | | 2 | | |
| 5 | QGENEEEDSGAIVTVK | 1703.99 | | 2 | | Glycinin G2 |
| 16 | NEGDVLV | 744.54 | | 2 | | Glycinin G5 |
| 17 | YNTGDEPVVA | 1063.52 | | 1 | | |
| 18 | HGKHEDDEDEDEEEDQPRPDHPPQRP | 3132.55 | | 1 | | |
| 19 | GKHEDDEDEDEEEDQPRPDHPPQRP | 2995.3 | | 1 | | |
| 20 | DDEDEDEEEDQPRPDHPPQRP | 2810.68 | | 1 | | |
| 21 | HEDDEDEDEEEDQPRPDHPPQRP | 2544.13 | | 2 | | |

TABLE 8-continued

Peptide sequences from soy glycinin identified in purified fractions from strains St. thermophilus 6 (M5G) and L. paracasei subsp paracasei 10 (M27G)

| SEQ ID No. | Peptide Sequence | Molecular weight(Da) | Fraction 6 strain 6 | Fraction 7 strain 6 | Fraction 6 strain 10 | Protein |
|---|---|---|---|---|---|---|
| 3 | EEDQPRFDHPPQRP | 1696.83 | | | 1 | |
| 22 | SGPLVNP | 682.58 | | | 1 | |

From these purified fractions, a total of 11 peptides were selected to be synthesized and evaluated in vivo in the obesity model of C. elegans (Table 9). All peptides were evaluated at 1 µg/mL of final concentration.

TABLE 9

Glycinin peptides selected for their in vivo evaluation with C. elegans.

| SEQ ID No. | Peptide Code | Sequence | Source | % Fluorescence Reduction C. elegans |
|---|---|---|---|---|
| 4 | P8a | SVIKPPTD | Strain 6 | 44.67 ± 10.5 |
| 2 | P6a | SDNFEY | Strain 6 | 40.90 ± 11.6 |
| 3 | P14c | EEDQPRPDHPPQRP | Strain 6 | 39.37 ± 7.08 |
| 5 | P16f | QGENEEEDSGAIVTVK | Strain 6 | 38.95 ± 8.7 |
| 6 | P14b | QGENEGEDKGAIVT | Strain 6 | 35.30 ± 6.1 |
| 1 | P10b | EEEGGSVLSG | Strain 10 | 33.48 ± 6.1 |
| 11 | P21b | GKREQDEDEDEDEDKPRPSRP | Strain 10 | 24.91 ± 7.1 |
| 12 | P15a | HQQEEENEGGSILSG | Strain 6 | 22.82 ± 6.1 |
| 8 | P16e | DEDEDEDEDKPRPSRP | Strain 6 | 21.86 ± 4 |
| 7 | P17c | QDEDEDEDEDKPRPSRP | Strain 10 | 18.13 ± 5.57 |
| 9 | P14d | DEDEDEDKPRPSRP | Strain 6 | 6.26 ± 7.6 |

Among them, peptides with capacity to reduce fat accumulation more than 30% were in vitro evaluated towards pancreatic lipase (PL) and phospholipase A2 (PLA2). In the case of PL, IC50 value was determined (Table 10) and in PLA2 study three different concentrations of each peptide were tested (Table 11).

TABLE 10

IC50 value of each peptide in PL enzymatic assay.

| SEQ ID No. | Peptide Code | Peptide sequence | PL IC50 (mg/ml) | Source |
|---|---|---|---|---|
| 1 | P10b | EEEGGSVLSG | 0.035 | Strain 10, glycinin |
| 2 | P6a | SDNFEY | 0.043 | Strain 6, glycinin |
| 3 | P14c | EEDQPRPDHPPQRP | 0.049 | Strain 6, glycinin |
| 4 | P8a | SVIKPPTD | 0.059 | Strain 6, glycinin |
| 5 | P16f | QGENEEEDSGAIVTVK | 0.447 | Strain 6, glycinin |
| 6 | P14b | QGENEGEDKGAIVT | 0.5 | Strain 6, glycinin |

TABLE 11

Percentage of PLA2 inhibition of each peptide at three different concentrations tested.

| Concentration (mg/ml) | (P6a) SEQ ID No. 2 | (P8a) SEQ ID No. 4 | (P10b) SEQ ID No. 1 | (P14b) SEQ ID No. 6 | (P14c) SEQ ID No. 3 | (P16f) SEQ ID No. 5 |
|---|---|---|---|---|---|---|
| 0.035 | 10.6 ± 5.0 | 12.7 ± 6.1 | 7.8 ± 5.6 | 5.9 ± 5.0 | 20.4 ± 4.4 | 13.6 ± 3.8 |
| 0.35 | 12.1 ± 4.0 | 12.9 ± 3.9 | 13.9 ± 3.3 | 22.2 ± 5.6 | 21.1 ± 4.3 | 13.6 ± 0.4 |
| 2 | 24.5 ± 1.4 | 26.0 ± 6.4 | 26.1 ± 5.9 | 23.8 ± 5.5 | 25.2 ± 4.3 | 15.9 ± 6.0 |
| 3.5 | 31.9 ± 5.5 | 20.1 ± 7.7 | 26.9 ± 2.5 | 28.8 ± 3.1 | 26.1 ± 4.1 | 22.5 ± 3.7 |

Identification of the Most Resistant Peptides Potentially Responsible of Fat Reduction An in vitro enzymatic digestion model of an in vivo digestive tract was developed for mimicking the physiological conditions to check and certify that each selected peptide was differently degraded throughout the gastro-intestinal tract by the digestive process. Pepsin, pancreatin and bile concentrations were optimized using a published experimental design (Granado-Lorencio et al (2007). J. Agri. Food. Chem., 55, 6387-6394).

By means of a high-performance liquid chromatography (HPLC), it was observed that the peptides P14c and P16f were completely degraded at the beginning of the intestinal phase, while P8a and P14b were resistant until the end of the process where they finally were degraded (Table 12).

TABLE 12

Percentage of peptides degradation in the in vitro digestion model.

| | Degradation (%) | | | | |
|---|---|---|---|---|---|
| | SEQ ID No. 2 P6a | SEQ ID No. 4 P8a | SEQ ID No. 6 P14b | SEQ ID No. 3 P14c | SEQ ID No. 5 P16f |
| Oral phase 5 min. | 23.7 | 1.7 | 6.0 | 5.3 | −1.2 |
| Gastric phase 30 min. | 31.0 | −1.3 | 6.7 | 4.2 | 65.8 |
| Gastric phase 120 min. | 66.9 | −1.0 | 8.7 | 4.6 | 95.2 |
| Intestinal phase 15 min. | 100 | 51.2 | 36.7 | 92.9 | 100.0 |
| Intestinal phase 30 min. | 100 | 71.6 | 48.9 | 93.2 | 100.0 |
| Intestinal phase 60 min. | 100 | 90.7 | 68.8 | 95.0 | 100.0 |
| Intestinal phase 120 min. | 100 | 100.0 | 100.0 | 95.5 | 100.0 |

The peptides of the present invention can be added to a food matrix either in isolated form or in the form of an extract. The peptides of the present invention can be added to the food matrix either alone or in the form of mixtures.

In a preferred embodiment the peptides may be obtained or manufactured by any method known in the art, including synthesis of the pure peptides and (isolated from) protein fractions generated by hydrolysis or fermentation as described in the present specification.

The peptides of the invention may be present in the food product as per se peptides (e,g from synthesizing the pure peptides) or as part of a protein fraction (e.g hydrolyzed or fermented protein).

In a particular embodiment of the present invention the peptides of the invention may be present in a food product as a result of adding the strains of the present invention in the corresponding food matrices containing soy glycinin.

Preferably this food product is a fermented product. The fermented product can be present in the form of a liquid or present in the form of a dry powder obtained by drying the fermented liquid.

Preferably the fermented product is a fresh and dairy product; more preferably fermented milk and/or fermented soy. Preferably the nutritional compositions are pasteurized and sterilized milks, yogurts and fermented milks, such as:

Dairy products, such as sterilized and/or pasteurized milk, yogurts, fermented milks, milk based desserts. Infant and follow-on formulas and baby foods. Fresh and/or pasteurized cheese. Vegetable products, such as, fruit juice products, syrups and/or fruit essences, marmalade, compote and/or jam. Soybean milk and/or extracts, tiger nuts, cereals, nuts and dried fruits, milk and fermented extracts based on soybean, fruits, nuts and dried fruits and cereals. Infant formulas based on milk, milk products, fruits, cereals, rice, baby foods, etc. Fresh, dried and/or freeze dried food supplements issued directly or through food products and specific preparations for the general population or people with weight problems or obesity. Enriched and/or supplemented water and drinks. In general, staple food and/or functional products which are susceptible to be enriched with functional peptides derived from base product fermentation, and/or extraction of functional peptides, to be added in food matrices as active ingredients.

The amount of the peptides according to the invention in the food product is preferably at least 0.01 g/kg, more preferably from 0.1 to 10 g/kg, even more preferably from 1 to 7 g/kg and most preferably from 3 to 7 g/kg of said peptides, for example 5 g/kg. Preferably the amount of peptides in these food products is chosen such that the amount of peptide per total amount of serving of the food product is from 0.01 to 1 g, preferably 0.1 to 1 g, more preferably 0.1 to 0.7 g and most preferably 0.2 to 0.5 g.

EXAMPLES

1. Formulation of a Food Product with the Peptides and Fat Reduction Effect

The objective of the present study was to evaluate the antiobesity effect of the more effective peptides obtained from glycinin after their addition to a food matrix. We selected 5 peptides obtained from hydrolysis of glycinin with strain 6 (P8a, P6a, P14c, P16f, P14b) The peptides from glycinin were added to a soy fermented product (Savia® from Danone) both alone or mixed at final concentration of 1 μg/mL. Nematodes were fed with these products and then total lipids were quantified by Nile Red staining.

Table 13 shows the level of fluorescence reduction in nematodes fed with soy fermented product containing the different glycinin peptides or their combination. Results indicate the in vivo effectiveness of all glycinin peptides when they are added to the soy fermented product. Combination of these 5 peptides in the food matrix also provided a significant reduction of fluorescence.

TABLE 13

Percentages of fluorescence reduction in nematodes fed with Savia ® (Danone) containing the selected glycinin peptides, P8a, P6a, P14c, P16f and P14b.

| Condition | % Fluorescence Reduction |
|---|---|
| NG-Orlistat | 29.5 ± 0.1 |
| NG-Savia | 7.9 ± 2.9 |
| NG-P8a | 41.7 ± 4.02 |
| NG-Savia + P8a | 29.8 ± 3.3 |
| NG-P6a | 36.2 ± 4.1 |
| NG-Savia + P6a | 29.5 ± 2.5 |
| NG-P14c | 33.7 ± 5.5 |
| NG-Savia + P14c | 22.5 ± 1.5 |
| NG-P16f | 33.9 ± 5.7 |
| NG-Savia + P16f | 28.82 ± 6.6 |
| NG-P14b | 30.25 ± 4.2 |
| NG-Savia + P14b | 27.42 ± 4.07 |
| NG-P8a + P6a + P14c + P16f + P14b | 28.13 ± 1.5 |
| NG-Savia + P8a + P6a + P14c + P16f + P14b | 29.2 ± 1.4 |

The invention claimed is:

1. A fermented milk food product comprising one or more peptides having pancreatic lipase (PL) and/or phospholipase A2 (PLA2) inhibiting activity obtained by hydrolysis of soy glycinin with at least one bacterial strain selected from the group consisting of *Streptococcus thermophilus* CNCM 1-2776, *Streptococcus thermophilus* CNCM I-1630, and *Lactobacillus paracasei* subsp *paracasei* CNCM 1-4270, wherein at least one of said peptides is a peptide selected from the group consisting of SEQ ID NOs: 1-12 and 14-22, and further comprising said at least one bacterial strain in a matrix containing soy glycinin.

2. The fermented milk food product according to claim 1, wherein the peptides are in the form of an extract.

3. The fermented milk food product according to claim 1, wherein the peptides are in isolated form.

4. The fermented milk food product according to claim 1, wherein the amount of said peptide per total amount of serving of the food products is from 0.01 to 1 g.

5. The fermented milk food product according to claim 1, comprising at least 0.01 g/kg of said peptides.

6. A method for producing peptides having pancreatic lipase (PL) and/or phospholipase A2 (PLA2) inhibiting activity, said method comprising hydrolyzing or fermenting soy glycinin with at least one bacterial strain selected from the group consisting of *Streptococcus thermophilus* CNCM 1-2776, *Streptococcus thermophilus* CNCM 1-1630, and *Lactobacillus paracasei* subsp *paracasei* CNCM I-4270, wherein at least one of said peptides is a peptide selected from the group consisting of SEQ ID NOs:1-12 and 14-22.

7. The fermented milk food product according to claim 1, wherein at least one of said peptides is a peptide selected from the group consisting of SEQ ID NOs: 1-6.

8. The fermented milk food product according to claim 1, wherein said fermented milk food product is a sterilized and/or a pasteurized fermented milk food product.

* * * * *